US011459314B2

United States Patent
Hemmer et al.

(10) Patent No.: US 11,459,314 B2
(45) Date of Patent: Oct. 4, 2022

(54) METHOD FOR ISOLATION OF AN AROMATIC DIANHYDRIDE AND AROMATIC DIANHYDRIDES PREPARED BY THE METHOD

(71) Applicant: SABIC GLOBAL TECHNOLOGIES B.V., Bergen op Zoom (NL)

(72) Inventors: Gregory L. Hemmer, Mt. Vernon, MI (US); Sivakumar Periyasamy, Bangalore (IN); Simon Padmanabhan, Mt. Vernon, MI (US); Robert Werling, Mt. Vernon, MI (US); Ravi Gautam, Bangalore (IN)

(73) Assignee: SHPP GLOBAL TECHNOLOGIES B.V., Bergen op Zoom (NL)

( * ) Notice: Subject to any disclaimer, the term of this patent is extended or adjusted under 35 U.S.C. 154(b) by 144 days.

(21) Appl. No.: 17/049,596

(22) PCT Filed: May 6, 2019

(86) PCT No.: PCT/US2019/030810
§ 371 (c)(1),
(2) Date: Oct. 22, 2020

(87) PCT Pub. No.: WO2019/217257
PCT Pub. Date: Nov. 14, 2019

(65) Prior Publication Data
US 2021/0371405 A1  Dec. 2, 2021

(30) Foreign Application Priority Data
May 7, 2018   (EP) .................................... 18171060

(51) Int. Cl.
*C07D 405/12*   (2006.01)
(52) U.S. Cl.
CPC ................. *C07D 405/12* (2013.01)
(58) Field of Classification Search
CPC .................................................. C07D 405/12
See application file for complete search history.

(56) References Cited

U.S. PATENT DOCUMENTS

| | | |
|---|---|---|
| 3,389,970 A | 6/1968 | Scheibel |
| 3,875,116 A | 4/1975 | Heath et al. |
| 3,956,320 A | 5/1976 | Heath et al. |
| 4,020,089 A | 4/1977 | Markezich |
| 4,116,980 A | 9/1978 | Webb |
| 4,217,281 A | 8/1980 | Markezich et al. |
| 4,257,953 A | 3/1981 | Williams, III et al. |
| 4,318,857 A | 3/1982 | Webb et al. |
| 4,329,291 A | 5/1982 | Webb et al. |
| 4,329,292 A | 5/1982 | Webb |
| 4,329,496 A | 5/1982 | Webb |
| 4,340,545 A | 7/1982 | Webb et al. |
| 4,417,044 A | 11/1983 | Parekh |
| 4,520,204 A | 5/1985 | Evans |
| 4,571,425 A | 2/1986 | Silva |
| 4,584,388 A | 4/1986 | Webb |
| 4,902,809 A | 2/1990 | Groeneweg et al. |
| 5,359,084 A | 10/1994 | Dellacoletta et al. |
| 6,008,374 A | 12/1999 | Dellacoletta et al. |
| 6,235,866 B1 | 5/2001 | Khouri et al. |
| 6,265,521 B1 | 7/2001 | Fyvie et al. |
| 6,498,224 B1 | 12/2002 | Odle et al. |
| 7,153,394 B2 | 12/2006 | Guggenheim et al. |
| 2006/0205958 A1 | 9/2006 | Brunelle et al. |
| 2009/0056793 A1 | 3/2009 | Langhals et al. |
| 2009/0247727 A1 | 10/2009 | Bernabe et al. |
| 2011/0319620 A1 | 12/2011 | Ishihara et al. |
| 2019/0040201 A1 | 2/2019 | Patil et al. |
| 2019/0092726 A1 | 3/2019 | Schulte, II et al. |
| 2019/0119240 A1 | 4/2019 | Royer et al. |
| 2019/0135750 A1 | 5/2019 | Croll et al. |

FOREIGN PATENT DOCUMENTS

| | | | |
|---|---|---|---|
| DE | 3213166 A1 | 10/1983 | |
| EP | 0477539 A1 | 4/1992 | |
| WO | 2017172593 A1 | 5/2017 | |
| WO | 2017189293 A1 | 11/2017 | |

OTHER PUBLICATIONS

International Search Report for International Application No. PCT/US2019/031972; International Filing Date May 13, 2019; dated Jul. 8, 2019; 8 pages.
International Search Report for International Application No. PCT/US2019/037182; International Filing Date Jun. 14, 2019; dated Aug. 26, 2019; 6 pages.
International Search Report for the corresponding International Application No. PCT/US2019/030810; International Filing Dtae: May 6, 2019; dated Jul. 30, 2019. 5 pages.
International Search Report for the corresponding International Application No. PCT/US2019/035325; International Filing Date: Jun. 4, 2019; dated Jul. 24, 2019. 6 pages.
Written Opinion for International Application No. PCT/US2019/031972; International Filing Date May 13, 2019; dated Jul. 8, 2019; 12 pages.

(Continued)

*Primary Examiner* — Paul V Ward
(74) *Attorney, Agent, or Firm* — Cantor Colburn LLP

(57) ABSTRACT

A method for producing an aromatic dianhydride includes reacting an aromatic diimide with a substituted or unsubstituted phthalic anhydride in an aqueous medium in the presence of an amine exchange catalyst to provide an aqueous reaction mixture including an N-substituted phthalimide, an aromatic tetraacid salt, and at least one of an aromatic triacid salt and an aromatic imide diacid salt. The method further includes removing the phthalimide from the aqueous reaction mixture by extracting the aqueous reaction mixture with an organic solvent using a sieve tray extraction column. The aromatic tetraacid salt is converted to the corresponding aromatic dianhydride. Aromatic dianhydrides prepared according to the method are also described.

16 Claims, No Drawings

(56) References Cited

OTHER PUBLICATIONS

Written Opinion for International Application No. PCT/US2019/037182; International Filing Date Jun. 14, 2019; dated Aug. 26, 2019; 9 pages.

Written Opinion for the corresponding International Application No. PCT/US2019/030810; International Filing Dtae: May 6, 2019; dated Jul. 30, 2019. 9 pages.

Written Opinion for the corresponding International Application No. PCT/US2019/035325; International Filing Date: Jun. 4, 2019; dated Jul. 24, 2019. 6 pages.

International Search Report for International Application No. PCT/US2017/028263; International Filing Date Apr. 19, 2017; dated Aug. 24, 2017; 6 pages.

Written Opinion of the International Searching Authority for International Application No. PCT/US2017/028263; International Filing Date Apr. 19, 2017; dated Aug. 24, 2017; 9 pages.

Basosca, I. et al., "Comparative study of polyimides containing different flexible linkages", J. Iran Chem. Soc., vol. 9, 2012; pp. 901-910.

Bruma, M. et al., "Polyetherimides for Gas Separation Membranes", Molecular Crystals and Liquid Crystals, vol. 418, pp. 11-19.

Hu, Yu Lin et al., "An inexpensive and efficient synthetic method for the preparation of pyromellitic dianhydride promoted by ionic liquid", ARKIVOC, vol. 9, 2010; pp. 63-74.

International Search Report for the corresponding International Application No. PCT/US2019/030810; International Filing Date: May 6, 2019; dated Jul. 30, 2019. 5 pages.

Pinzow, Leonard, "Characteristics of a pulsed packed, liquid-liquid extraction column", Calhoun: The NPS Institutional Archive, Retrieved from the Internet on Sep. 20, 2018; http://hdl.handle.net/10945/13989; Jan. 1, 1957; pp. 1-105.

Rauber, Johannes, "Design Practice for Packed Liquid Liquid Extraction Columns", Sulzer, Retrieved from the Internet on Sep. 20, 2018; http://folk.ntnu.no/skoge/prost/proceedings/aiche-2006/data/papers/P73337.pdf; Jan. 1, 2006; pp. 1-12.

Schwartz, W. T., "A Novel Route to Aryl Diether Dianhydrides", High Performance Polymers, vol. 2, No. 3, 1990; pp. 189-196.

Wei, Haibing et al., "Comparative Study on Polyimides from Isomeric 3,3'-, 3,4'-, and 4,4'-Linked Bis(thioether anhydride)s", Journal of Polymer Science Part A: Polymer Chemistry, vol. 49, 2011; pp. 2484-2494.

Written Opinion for the corresponding International Application No. PCT/US2019/030810; International Filing Date: May 6, 2019; dated Jul. 30, 2019; 9 pages.

Yoon, Chong-Bok et al., "Facile synthesis of new NLO-functionalized polyimides via Mitsunobu reaction", Journal Material Chemistry, vol. 9; 1999; pp. 2339-2344.

METHOD FOR ISOLATION OF AN AROMATIC DIANHYDRIDE AND AROMATIC DIANHYDRIDES PREPARED BY THE METHOD

CROSS-REFERENCE TO RELATED APPLICATIONS

This application is a National Stage application of PCT/US2019/030810, filed May 6, 2019, which claims the benefit of European Application No. 18171060.9 filed on May 7, 2018, both of which are incorporated by reference herein in their entirety.

BACKGROUND

Polyetherimides are a class of high performance polymers that can be processed to make molded articles, fibers, films, foams, and the like. Polyetherimides further have high strength, toughness, heat resistance, modulus, and broad chemical resistance, and so are widely used in industries as diverse as automotive, telecommunication, aerospace, electrical/electronics, transportation, and healthcare. Polyetherimides have shown versatility in various manufacturing processes, proving amenable to techniques including injection molding, extrusion, and thermoforming, to prepare various articles.

A number of processes for making polyetherimides have been disclosed. Two processes which have been of particular interest are the so-called melt polymerization and solution polymerization processes. Solution polymerization is generally conducted by reacting an aromatic dianhydride and an organic diamine in an inert solvent at elevated temperatures to form an amide-acid polymer via ring opening of the anhydride by nucleophilic attack of the diamine. The polyamide-acid is then formed into a polyetherimide by removal of water, for example by azeotropic distillation.

Aromatic dianhydrides are thus important to the production of polyetherimides. The aromatic dianhydrides can be prepared using an exchange reaction between an aromatic bisimide and a substituted or unsubstituted phthalic anhydride. In addition to dianhydride, the exchange reaction often produces various by-products which result in decreased yields of the dianhydride.

Accordingly, there remains a need for an improved method for producing and isolating dianhydrides that can provide high yields and minimize by-product formation.

BRIEF DESCRIPTION

A method for producing an aromatic dianhydride comprises reacting an aromatic diimide with a substituted or unsubstituted phthalic anhydride in an aqueous medium in the presence of an amine exchange catalyst at a reaction temperature of 140 to 250° C. and a reaction pressure of 150 to 300 psig, to provide an aqueous reaction mixture comprising an N-substituted phthalimide, an aromatic tetraacid salt, and at least one of an aromatic triacid salt and an aromatic imide diacid salt; removing the phthalimide from the aqueous reaction mixture by extracting the aqueous reaction mixture with an organic solvent using a single extraction column, wherein the extraction column is a sieve tray extraction column; and converting the aromatic tetraacid salt to the corresponding aromatic dianhydride.

An aromatic dianhydride prepared by the above method has an imide anhydride content of 2 weight percent or less.

The above described and other features are exemplified by the following detailed description.

DETAILED DESCRIPTION

The present inventors have discovered that use of a modified extraction procedure for isolation of an aromatic dianhydride can increase the overall dianhydride conversion and yield. Specifically, the dianhydride conversion and yield can be increased at a particular phthalic anhydride to aromatic bisimide molar ratio, as discussed herein. In particular, the extraction procedure for isolation of an aromatic dianhydride of the present disclosure includes a sieve tray extraction column. The isolated aromatic dianhydrides advantageously have reduced amounts of imide anhydride by-products, which can facilitate production of high molecular weight poly(etherimide).

Accordingly, a method for producing an aromatic dianhydride represents one aspect of the present disclosure. The method comprises reacting an aromatic bisimide with a substituted or unsubstituted phthalic anhydride in an aqueous medium in the presence of an amine exchange catalyst and under conditions effective to provide an aqueous reaction mixture.

The aromatic bisimide can be of the formula (1)

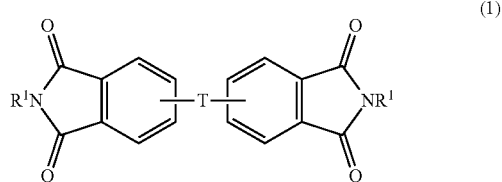

wherein T is —O—, —S—, —C(O)—, —SO$_2$—, —SO—, —C$_y$H$_{2y}$— wherein y is an integer from 1 to 5 or a halogenated derivative thereof or —O—Z—O—, wherein Z is an aromatic C$_{6-24}$ monocyclic or polycyclic moiety optionally substituted with 1 to 6 C$_{1-8}$ alkyl groups, 1 to 8 halogen atoms, or a combination comprising at least one of the foregoing. In an aspect, the R$^1$ is a monovalent C$_{1-13}$ organic group.

In an aspect, T is —O— or a group of the formula —O—Z—O— wherein the divalent bonds of the —O— or the —O—Z—O— group are in the 3,3', 3,4', 4,3', or the 4,4' positions. Exemplary groups Z include groups of formula (2)

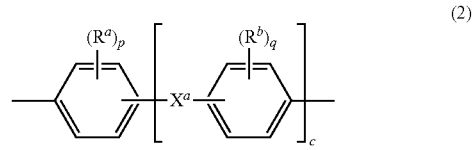

wherein R$^a$ and R$^b$ are each independently the same or different, and are a halogen atom or a monovalent C$_{1-6}$ alkyl group, for example; p and q are each independently integers of 0 to 4; c is 0 to 4; and X$^a$ is a bridging group connecting the hydroxy-substituted aromatic groups, where the bridging group and the hydroxy substituent of each C$_6$ arylene group are disposed ortho, meta, or para (specifically para) to each other on the C$_6$ arylene group. The bridging group X$^a$ can be a single bond, —O—, —S—, —S(O)—, —S(O)$_2$—, —C(O)—, or a $C_{1-18}$ organic bridging group. The $C_{1-18}$ organic bridging group can be cyclic or acyclic, aromatic or non-aromatic, and can further comprise heteroatoms such as halogens, oxygen, nitrogen, sulfur, silicon, or phosphorous. The $C_{1-18}$ organic group can be disposed such that the $C_6$ arylene groups connected thereto are each connected to a common alkylidene carbon or to different carbons of the $C_{1-18}$ organic bridging group. A specific example of a group Z is a divalent group of the formula (3a) or (3b)

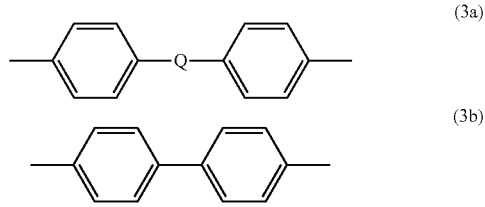

wherein Q is —O—, —S—, —C(O)—, —SO$_2$—, —SO—, —P(R$^a$)(=O)— wherein R$^a$ is a $C_{1-8}$ alkyl or $C_{6-12}$ aryl, or —C$_y$H$_{2y}$— wherein y is an integer from 1 to 5 or a halogenated derivative thereof (including a perfluoroalkylene group). Exemplary dihydroxy aromatic compounds from which Z can be derived include but are not limited to 2,2-bis(2-hydroxyphenyl)propane, 2,4'-dihydroxydiphenylmethane, bis(2-hydroxyphenyl)methane, 2,2-bis-(4-hydroxyphenyl)propane ("bisphenol A" or "BPA"), 1,1-bis-(4-hydroxyphenyl)ethane, 1,1-bis-(4-hydroxyphenyl)propane, 2,2-bis-(4-hydroxyphenyl)pentane, 3,3-bis-(4-hydroxyphenyl)pentane, 4,4'-dihydroxybiphenyl, 4,4'-dihydroxy-3,3,5,5'-tetramethylbiphenyl, 2,4'-dihydroxybenzophenone, 4,4'-dihydroxydiphenylsulfone, 2,4'-dihydroxydiphenylsulfone, 4,4'-dihydroxydiphenylsulfoxide, 4,4'-dihydroxydiphenylsulfide, hydroquinone, resorcinol, 3,4-dihydroxydiphenylmethane, 4,4'-dihydroxybenzophenone, 4,4'-dihydroxydiphenylether, and the like, or a combination comprising at least one of the foregoing. In an aspect, Z is derived from bisphenol A, such that Q in the above formula is, 2,2-isopropylidene. Thus in an aspect, Z is 2,2-(4-phenylene)isopropylidene. In an aspect, R$^1$ is a $C_{1-4}$ alkyl group, for example a methyl group, an ethyl group, a propyl group, or a butyl group, preferably a methyl group.

In an aspect, the aromatic bisimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing.

The substituted or unsubstituted phthalic anhydride can be of the formula (4)

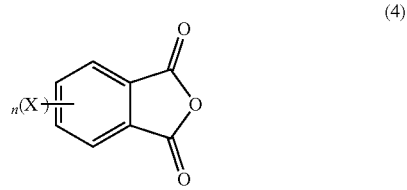

wherein X is fluoro, chloro, bromo, iodo, nitro, or a combination comprising at least one of the foregoing, and n is 0 or 1. In an aspect, n is 0 and the phthalic anhydride is an unsubstituted phthalic anhydride. In an aspect, n is 1, and the phthalic anhydride is a substituted phthalic anhydride, wherein X is fluoro, chloro, bromo, iodo, nitro, or a combination comprising at least one of the foregoing. In an aspect, the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing. Specific examples of suitable halophthalic anhydrides include 3-fluorophthalic anhydride, 4-fluorophthalic anhydride, 3-chlorophthalic anhydride, 4-chlorophthalic anhydride, 3-bromophthalic anhydride, 4-bromophthalic anhydride, 3-iodophthalic anhydride, and 4-iodophthalic anhydride. In an aspect, the substituted or unsubstituted phthalic anhydride is preferably phthalic anhydride.

Reacting the aromatic bisimide with the substituted or unsubstituted phthalic anhydride is carried out in aqueous medium in the presence of an amine exchange catalyst. The amine exchange catalyst can include a ($C_{1-20}$ alkyl)-substituted amine, preferably a tri($C_{1-20}$ alkyl)amine. In an aspect, the amine exchange catalyst is preferably trimethylamine, trimethylamine, or a combination comprising at least one of the foregoing. In as aspect, the initial molar ratio of amine exchange catalyst to the phthalic anhydride is 1:1 to 2:1.

The reacting is further carried out under conditions effective to provide an aqueous reaction mixture. Effective conditions can include reacting at a reaction temperature that is 140 to 250° C., for example 160 to 200° C., and a reaction pressure of 150 to 300 psig (1.13 to 2.16 megapascals (MPa)), preferably 200 to 250 psig (1.48 to 1.82 MPa), more preferably 200 to 230 psig (1.48 to 1.68 MPa).

In an aspect, the initial molar ratio of phthalic anhydride to aromatic bisimide is 4:1 to 20:1, or 4:1 to 10:1, or 4:1 to 8:1, or 4:1 to 5.5:1, or 4:1 to 5:1. Without wishing to be bound by theory, it is believed that a molar ratio of phthalic anhydride to aromatic bisimide of 4:1 to 5:1 is preferred at least for economic reasons.

In an aspect, the aqueous reaction mixture can have a solids content of 5 to 26 weight percent, or 10 to 20 weight percent, or 13 to 23 weight percent, or 13 to 17 weight percent, or 13 to 16 weight percent. As used herein, the term "solids content" is defined as the weight of the aromatic diimide, the aromatic dianhydride, and, when present, the aromatic imide-anhydride, the aromatic tetra acid salt, the aromatic triacid salt, the aromatic imide-diacid salt, and the corresponding ring-closed derivatives thereof, relative to the total weight of the reaction mixture. Advantageously, when using the solids content described herein, the process can use reduced amounts of water compared to prior processes. Thus the presently disclosed process can be a more sustainable process.

The aqueous reaction mixture provided by reacting the aromatic bisimide with the substituted or unsubstituted phthalic anhydride comprises an N-substituted phthalimide, an aromatic tetraacid salt, and at least one of an aromatic triacid salt and an aromatic imide diacid salt.

In an aspect, the aromatic tetra acid salt is of the formula (5)

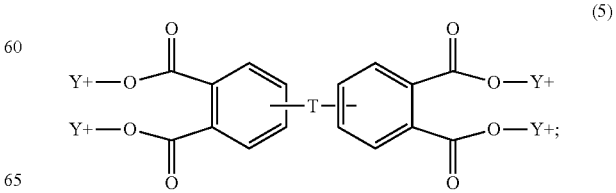

the aromatic triacid salt is of the formula (6)

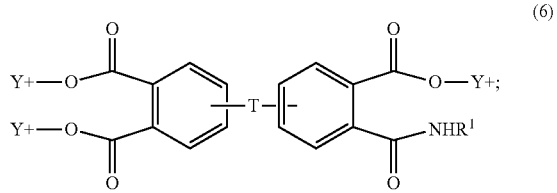

and the aromatic imide-diacid salt is of the formula (7)

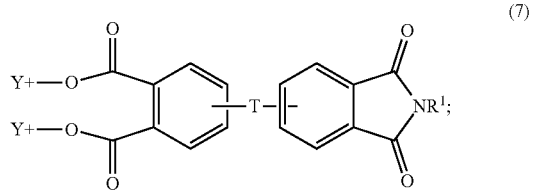

wherein T can be as described above, and is preferably —O—, —S—, —C(O)—, —SO$_2$—, —SO—, —C$_y$H$_{2y}$— wherein y is an integer from 1 to 5 or a halogenated derivative thereof or —O—Z—O—, wherein Z is an aromatic C$_{6-24}$ monocyclic or polycyclic moiety optionally substituted with 1 to 6 C$_{1-8}$ alkyl groups, 1 to 8 halogen atoms, or a combination comprising at least one of the foregoing, R$^1$ is a C$_{1-13}$ organic group, or a C$_{1-4}$ alkyl group, preferably a methyl group, and Y is a cationic group, preferably a C$_{1-20}$ trialkylammonium group, or a proton (i.e., the aromatic tetraacid salt, triacid salt, and imide diacid salt can be in the form of the corresponding aromatic tetraacid, triacid, and imide acid, respectively). In an aspect, Y is a C$_{1-20}$ trialkylammonium group, preferably a triethylammonium group. Thus, in an aspect, the aromatic tetra acid salt can be an aromatic tetra acid triethylamine salt, the aromatic triacid salt can be an aromatic triacid triethylamine salt, and the aromatic imide-diacid salt can be an aromatic imide-diacid triethylamine salt. In an aspect, T is —O—Z—O—, wherein Z is derived from bisphenol A. The divalent bonds of the —O—Z—O— group are in the 3,3', 3,4', 4,3', or the 4,4' positions.

In an aspect, the aqueous reaction mixture can further comprise at least one of the aromatic bisimide and the substituted or unsubstituted phthalic anhydride. In an aspect, the aqueous reaction mixture can further comprise the substituted or unsubstituted phthalic anhydride, preferably wherein the substituted or unsubstituted phthalic anhydride is in the form of the corresponding ring-opened diacid salt.

The method further comprises removing the N-substituted phthalimide and any residual aromatic bisimide from the aqueous reaction mixture by extracting the aqueous reaction mixture with an organic solvent. In an aspect, the organic solvent is a (C$_{1-6}$ alkyl)benzene, benzene, or a halogenated aromatic solvent. For example, the organic solvent can comprise toluene, xylene, chlorobenzene, ortho-dichlorobenzene, or a combination comprising at least one of the foregoing. In an aspect, the organic solvent can optionally comprise 0 to 15 weight percent, or 1 to 10 weight percent, or 2 to 8 weight percent of a tri(C$_{1-6}$ alkyl)amine, preferably triethylamine.

The extracting to remove the N-substituted phthalimide and any residual aromatic bisimide is in a sieve tray extraction column (i.e., wherein the extraction column contains sieve tray packing). When using the sieve tray extraction column, the aqueous phase from the exchange reaction is typically fed into the top of the sieve tray extraction column while the organic solution is fed into the bottom of the sieve tray extraction column. In an aspect, the volumetric ratio of the organic solvent to aqueous medium is 0.3:1 to 2:1, or 0.5:1 to 1:1, or 0.75:1 to 1:1.

The present inventors have advantageously discovered that various process parameters can be adjusted in order to achieve the desired conversion to the aromatic dianhydride at the phthalic anhydride to aromatic bisimide molar ratios given above. For example, the sieve tray extraction column can have a capacity of 220 gallons per hour per square foot or more, preferably 500 gallons per hour per square foot or more (20.37 (m$^3$/hr)/m$^2$ or more), for example, 500 to 700 gallons per hour per square foot, or 220 to 60 gallons per hour per square foot. As used herein, the capacity in gallons per hour per square foot is the sum of the aqueous and organic flow rates. In an aspect, this can correspond to an aqueous flow rate of at least 34 kilograms per hour.

In an aspect, the dispersed phase holdup can be at least 5%, preferably at least 10%. As used herein, the term "dispersed phase holdup" refers to a measure of the volume of the dispersed phase in the column compared to the total volume of the liquid in the column. Accordingly, for example, a dispersed phase holdup of at least 5% means that at least 5% of the total volume of liquid in the column is the dispersed phase. The dispersed phase comprises the organic solution, thus the column comprises droplets of the organic solution dispersed in a continuous phase comprising the aqueous phase. In an aspect, the dispersed phase can be less than or equal to 50%, or less than or equal to 40%, or less than or equal to 20%, or less than or equal to 15%. Advantageously, as further described in the working examples below, a higher dispersed phase hold up can provide greater than 95% extraction efficiency of phthalimide and aromatic bisimide with an aqueous phase residence time of less than 30 minutes, and can also provide the desired aromatic dianhydride have a particular imide anhydride content (i.e., less than 2 weight percent).

The sieve tray extraction column can comprise, for example, at least 50 trays with a tray spacing of 75 to 125 millimeters (mm), or 90 to 110 mm, or 95 to 105 mm, or about 100 mm.

The extracting is carried out at an extraction temperature of 100 to 200° C., for example 110 to 180° C., or 115 to 175° C. The extracting can be for a period of time of, for example, 30 seconds to 3 hours, or 5 minutes to 3 hours, or 20 minutes to 3 hours, or 20 minutes to 2 hours, or 20 minutes to 1 hour, or 1 to 3 hours, or 1 to 2 hours, or 1 to 1.5 hours, preferably 5 minutes to 3 hours, or 20 minutes to 2 hours, or 20 minutes to 1 hour. The extracting of the present disclosure is advantageously conducted in a single extraction column.

In an aspect, conversion of the aromatic bisimide to an aromatic tetraacid salt can be greater than 70%, or greater than 75%, or greater than 78% or greater than 80% after the extraction step (i.e., upon exiting the extraction column). In an aspect, conversion of the aromatic bisimide to aromatic tetraacid salt can be 70 to 90%, or 75 to 90%, or 78 to 90%, or 80 to 90% after the extraction step.

In an aspect, the extracting provides an extracted aqueous stream comprising the aromatic tetraacid salt and optionally the aromatic triacid salt, the aromatic imide-diacid salt, a substituted or unsubstituted phthalic acid salt, or a combination comprising at least one of the foregoing, and an organic stream comprising the organic solvent, N-substituted phthalimide, and any residual aromatic bisimide.

The method further comprises converting the aromatic tetraacid salt to the corresponding aromatic dianhydride. Converting the aromatic tetraacid salt to the corresponding aromatic dianhydride occurs in separate equipment positioned downstream of the extraction column. The amount of time as well as the temperature for the converting is generally dependent upon the identity of the dianhydride and can be readily determined by one of ordinary skill in the art. For example, useful temperatures can be 160 to 300° C., or 180 to 240° C. or 200 to 220° C. The conversion of the aromatic tetraacid salt to dianhydride is a cyclization with the concurrent formation of water and evolution of a free amine species derived from the cationic group Y. For example, the tetraacid salt can be condensed by refluxing in the presence of a dehydrating agent, for example acetic anhydride. In an aspect, a temperature of 100 to 225° C. and a pressure of 0 MPa to 1 MPa can be used. The aromatic dianhydride can optionally be isolated using any isolation techniques that are generally known, for example, filtration. Advantageously, trace water, catalyst, and other residual volatile materials such as phthalic anhydride can also be removed as vapor under the conditions utilized for conversion. In an aspect, the converting can provide a product mixture comprising the aromatic dianhydride and an aromatic imide-anhydride, for example formed from the cyclization of the above-described aromatic triacid salt.

The aromatic dianhydride can be of the formula (8)

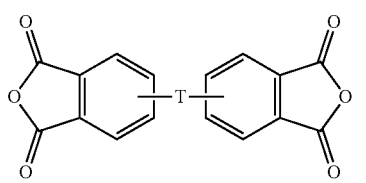

wherein T can be as defined above. In an aspect, T is —O—Z—O—, preferably wherein Z is derived from bisphenol A (i.e., Z is 2,2-(4-phenylene)isopropylidene). Illustrative examples of aromatic dianhydrides include 3,3-bis[4-(3,4-dicarboxyphenoxy)phenyl]propane dianhydride; 4,4'-bis(3,4-dicarboxyphenoxy)diphenyl ether dianhydride; 4,4'-bis(3,4-dicarboxyphenoxy)diphenyl sulfide dianhydride; 4,4'-bis(3,4-dicarboxyphenoxy)benzophenone dianhydride; 4,4'-bis(3,4-dicarboxyphenoxy)diphenyl sulfone dianhydride; 2,2-bis[4-(2,3-dicarboxyphenoxy)phenyl]propane dianhydride; 4,4'-bis(2,3-dicarboxyphenoxy)diphenyl ether dianhydride; 4,4'-bis(2,3-dicarboxyphenoxy)diphenyl sulfide dianhydride; 4,4'-bis(2,3-dicarboxyphenoxy)benzophenone dianhydride; 4,4'-bis(2,3-dicarboxyphenoxy)diphenyl sulfone dianhydride; 4-(2,3-dicarboxyphenoxy)-4'-(3,4-dicarboxyphenoxy)diphenyl-2,2-propane dianhydride; 4-(2,3-dicarboxyphenoxy)-4'-(3,4-dicarboxyphenoxy)diphenyl ether dianhydride; 4-(2,3-dicarboxyphenoxy)-4'-(3,4-dicarboxyphenoxy)diphenyl sulfide dianhydride; 4-(2,3-dicarboxyphenoxy)-4'-(3,4-dicarboxyphenoxy)benzophenone dianhydride; and, 4-(2,3-dicarboxyphenoxy)-4'-(3,4-dicarboxyphenoxy)diphenyl sulfone dianhydride.

The aromatic imide-anhydride can be of the formula (9)

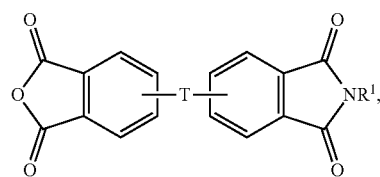

wherein T and $R^1$ are as defined above. In an aspect, T is —O—Z—O—, wherein Z is derived from bisphenol A. In an aspect, $R^1$ is preferably a methyl group.

In an aspect, overall conversion of the aromatic bisimide to an aromatic dianhydride can be greater than 70%, or greater than 75%, or greater than 78% or greater than 80%. In an aspect, conversion of the aromatic bisimide to aromatic dianhydride can be 70 to 90%, or 75 to 90%, or 78 to 90%, or 80 to 90%. In an aspect, the conversion of the aromatic bisimide to the aromatic dianhydride recited herein can be at a phthalic anhydride to aromatic bisimide molar ratio of 4:1 to 5.5:1 and a solids content of 10 to 20 weight percent, or 13 to 17 weight percent.

The above-described method can be carried out as a batchwise method or a continuous method.

In an aspect, the method comprises reacting an aromatic bisimide with a substituted or unsubstituted phthalic anhydride in an aqueous medium in the presence of an amine exchange catalyst at a reaction temperature that is 160 to 200° C. to form an aqueous reaction mixture; removing the N-substituted phthalimide and any residual aromatic bisimide from the aqueous reaction mixture by extracting with an organic solvent at an extraction temperature that is 160 to 200° C.

An aromatic dianhydride prepared according to the above-described method is another aspect of the present disclosure. The aromatic dianhydride can be of formula (8) above. Advantageously, the aromatic dianhydride can have an imide anhydride content of less than 2 weight percent, based on the total weight of the aromatic dianhydride. This is a particularly advantageous feature of the present disclosure because imide anhydride is a monofunctional reactant from the standpoint of a polymerization to form poly(etherimide). Thus, any imide anhydride present will act as a chain stopper during a polymerization reaction, making it difficult to achieve high molecular weight poly(etherimide). High molecular weight poly(etherimide) can provide many advantages, thus providing a higher purity aromatic dianhydride which in particular includes very low amounts of imide anhydride chain stopper is especially advantageous.

An improved method for isolation of an aromatic dianhydride is provided herein wherein a sieve tray extraction column is employed. The method advantageously employs extracting at carefully selected extraction conditions in order to increase overall conversion to dianhydride and increase the yield of the isolated aromatic dianhydride. In particular, overall conversion can be increased when a particular phthalic anhydride:aromatic bisimide molar ratio and a particular solids content are employed, as described herein. Therefore, a substantial improvement in methods of isolating an aromatic dianhydride is provided by the present disclosure.

This disclosure is further illustrated by the following examples, which are non-limiting.

EXAMPLES

Experiments were conducted using a 4 inch pilot sieve tray extraction column to study the efficiency of separating N-methylphthalimide and 4,4'-bisphenol A-bis-N-methylphthalimide (which can also include small amounts of 3,4'-bisphenol A-bis-N-methylphthalimide and 3,3'-bisphenol A-bis-N-methylphthalimide) from 4,4'-bisphenol A dianhydride. For simplicity of the discussion that follows, "N-methylphthalimide" will be referred to as "PI", the "4,4'-bisphenol A-bis-N-methylphthalimide" mixture will be referred to as "BI", and the "4,4'-bisphenol A dianhydride" product will be referred to as "DA".

Reaction of the BI with phthalic anhydride ("PA") was conducted at a molar ratio of 1:5 at a temperature of 160-165° C. at a pressure of 160 psig for 1 hour in the presence of triethylamine exchange catalyst. The molar ratio of triethylamine to PA was 1.5:1. Water was used at the solvent to provide an aqueous reaction mixture having the following composition: 6.43 wt % of PI, 14.6 wt % of PA, 8.955 wt % of DA, 4.566% of the corresponding imide anhydride ("IA"), 0.923 wt % BI, 43.8 wt %, water, and 20.74 wt % triethylamine, wherein weight percent of each component is based on the total weight of the aqueous reaction mixture. The solids content was maintained at 14 to 15 wt %. This composition of the aqueous reaction mixture corresponds to the following molar fractions: 0.627 DA, 0.312 IA, and 0.06 BI.

The aqueous mixture was fed to the top of the exchange column (i.e., the sieve tray column) at a desired flow rate, and the organic solvent used in the extraction was fed to the bottom of the column. The organic solvent used for extraction in the present examples was toluene including triethylamine in an amount of 4 to 5 weight percent.

Table 1 below shows a summary of the experiments using the sieve tray column with different flow rates of the aqueous reaction mixture entering the column.

In Table 1, "Capacity" refers to the total flow into the column (e.g., flow of the combined aqueous and organic streams) per unit area. "Aqueous flow rate" refers to the rate at which the aqueous phase enters the column from the reactor. "Organic flow rate" refers to the rate at which the organic phase enters the column. "IA lost to organic" refers to the amount of imide-anhydride species that is solubilized in the organic phase, and thus extracted from the column with PI and BI. "IA lost to back rxn" refers to the amount of the imide-anhydride species that is converted back to BI starting material, and then extracted into the organic phase and removed from the column. "IA to DA" refers to the conversion of the imide-anhydride species to the desired dianhydride tetra-acid salt. "IA remaining in aq" refers to the amount of imide-anhydride species that remains in the IA form in the aqueous phase during the extraction. "BI extraction efficiency" and "PI extraction efficiency" refer to the percentage of BI and PI, respectively, that are removed from the column during the extraction based on inlet feed compositions. It is noted that some small amount of BI or PI or both can remain in the aqueous phase.

The results show that ≥95% of N-methylphthalamide (PI) and ≥95% of bisimide (BI) extraction efficiency was achievable using a sieve tray column for the exchange reaction. It is noted that the amount of DA produced is constant. The amount of IA lost to back reaction (i.e., to revert to BI) and the amount of IA found in the extracted aqueous stream was tracked.

TABLE 1

| Ex | Capacity (gph/sqft) | Aqueous flowrate (kg/hr) | Organic flowrate (kg/hr) | Temp. (° C.) | IA lost to organic (mol %) | IA lost to back rxn (mol %) | IA to DA (mol %) | IA remaining in aq (mol %) | BI extraction efficiency (wt %) | PI extraction efficiency (wt %) |
|---|---|---|---|---|---|---|---|---|---|---|
| 1 | 500 | 105 | 53 | 120 | 6 | 8 | 7 | 79 | 95 | 96.2 |
| 2 | 500 | 79 | 72 | 120 | 2 | 8 | 28 | 62 | 98 | 95.7 |

Additional experiments were conducted using a 4-inch pilot sieve tray extraction column to study the effect of various parameters on the reaction efficiency (e.g., the amount of imide anhydride (IA) intermediate lost to back reaction). The reaction was conducted using a BLPA molar ratio of 1:4.2 and a PA:triethylamine molar ratio of 1:1.25. The aqueous reaction mixture outlet of a reactor was preheated and fed into the top of the sieve tray extraction column. Toluene was also preheated, and fed into the bottom of the extraction column. The aqueous reaction mixture feed entered the extraction column with the following composition: 6.16 wt % PI, 11.534 wt % PA, 7.828 wt % DA, 5.280 wt % IA, 1.280 wt % BI, 14.6 wt % triethylamine, and 53.4 wt % water. The solids content was maintained at 14 to 15 wt %. This composition of the aqueous reaction mixture corresponds to the following molar fractions: 0.551 DA, 0.363 IA, 0.086 BI.

Results from three experiments which varied certain parameters are shown in Table 2. "Dispersed phase holdup" in Table 2 refers to the volumetric holdup in the column (i.e., the amount of the total volume of the liquid in the column that is the dispersed phase). As noted above for Table 1, the amount of DA produced is constant. The amount of IA lost to back reaction (i.e., to revert to BI) and the amount of IA found in the extracted aqueous stream was tracked.

TABLE 4

| Ex. | Capacity (gph/sq. ft) | Aqueous flowrate (kg/hr) | Organic flowrate (kg/hr) | Residence time of aqueous (min) | Dispersed phase holdup (vol %) | Temp. (° C.) | IA lost to organic (mol %) | IA lost to back rxn (mol %) | IA remaining in aq (mol %) | IA to DA (mol %) | BI extraction efficiency (wt %) | P I extraction efficiency (wt %) | IA relative to DA (wt %) |
|---|---|---|---|---|---|---|---|---|---|---|---|---|---|
| 3 | 690 | 106.4 | 95.5 | 28 | 10 | 170-174 | 0.2 | 17 | 3 | 80 | 97.2 | 98.8 | 1.29 |
| 4 | 790 | 109.3 | 131 | 18 | 12 | 170-174 | 0.7 | 11 | 10 | 78 | 96.5 | 98.2 | 4.39 |
| 5 | 570 | 105.1 | 66.3 | 26 | 5 | 170-174 | 0.3 | 27 | 3 | 70 | 97 | 98.5 | 1.34 |

The experimental results in Table 2 show that imide anhydride lost to back reaction varies from 11 to 27% (based on the initial amount of IA that enters the exchange column) depending on the toluene flow rate, dispersed phase holdup, and other process parameters. Dispersed phase velocity is calculated based on the dispersed phase flowrate. Higher dispersed phase velocity will lead to a higher dispersed phase holdup, and result in a lower imide anhydride amount lost to back reaction. Results show that the dispersed phase velocity of 0.5 cm/s in the 4 inch column and a dispersed phase hold up of 12% leads to only 11% imide anhydride lost to back reaction. This represents a significant advantageous feature of the present method, as typical packed column processes tend towards a 50% loos of IA due to back reaction during extraction Limiting the imide anhydride loss to 11% allows for the yield of dianhydride to be increased to 80%.

Overall dianhydride molar yield can be calculated by adding the moles of DA that enter the extraction column (as this will not change during the course of the extraction) and the moles of IA converted to DA. For example, when 80% of the IA is converted to DA (as in Example 3 in Table 2 above), the overall DA yield can be calculated as 0.551 moles of DA+(0.363 moles of IA*0.8 moles of IA converted to DA). Thus, the product stream of example 3 achieves 84% conversion to DA (0.551+(0.363*0.8)=0.8414*100=84.14% DA).

As a Comparative Example, the process of the present disclosure using a sieve tray column was compared to a method using an extraction with a single packed extraction column. The packing was GOODLOE packing. Reaction was carried out at a PA:BI molar ratio of 4.5:1 to 5:1 at a triethylamine TEA:PA molar ratio of 2:1. Solids content (% solids) was maintained in the range of 13 to 15%. The reaction was conducted at 170° C. at a pressure of 230 psig with a residence time of 1 hour. The aqueous feed was fed to the top of GOODLOE packed extraction column, and toluene containing 5 weight percent (wt %) TEA was fed to the bottom of extraction column. The aqueous feed composition entering the extraction column was 45 mol % dianhydride as triethylammonium salts, 40 mol % IA as triethylammonium salts, and 15 mol % BI, all based on BI mole equivalents used in the reaction. Extraction was carried out with a temperature range of 145 to 170° C. with the pressure range of 200 to 250 psig.

Results from three comparative examples are shown in Table 3 below. Table 3 shows the amount of IA lost to back reaction (33 to 45 mole percent) and the resulting average molar conversion of BI to DA (67 to 72%). As discussed above, the use of the sieve tray extraction column resulted in 11 to 20 mole percent back reaction with a molar conversion of 80 to 83.5% BI to DA. Without wishing to be bound by theory, it is believed that the differences between the inventive examples and comparative examples can, at least in part, be attributed to the extraction in the comparative examples being less efficient, causing more BI to be formed, which cannot be converted to DA. Thus, the increased conversion of IA to DA to the sieve tray column is believed to be due to the increased extraction efficiency.

TABLE 3

| Comparative Example | Organic:Aqueous ratio (Vol) | Maximum capacity (gph/Sq. ft) | Minimum capacity (gph/sq. ft) | IA lost to back rxn (mol %) | BI to DA Conversion (mol %) | IA relative DA (wt %) |
|---|---|---|---|---|---|---|
| C1 | 1.4 | 361.26 | 177.24 | 33 | 72 | 2.5 |
| C2 | 1.2 | 358.02 | 155.1 | 38 | 70 | 2.5 to 3 |
| C3 | 1 | 325.44 | 141 | 45 | 67 | 2.5 to 3 |

An additional advantageous feature of the sieve tray column as compared to a packed extraction column is the improvement with regard to the flooding point. As used herein, "flooding point" refers to the capacity at which phase inversion (i.e., a reversal in which phase constitutes the continuous and dispersed phases), carryover (i.e., the aqueous phase is removed from the top of the column), or both, can occur. A packed extraction column has a flood capacity of about 600 gallons per hour per square foot (gph/sqft). As shown in Tables 1 and 2, experiments were conducted at higher capacity using a sieve tray column. The results above indicate that the sieve tray column can be operated at higher capacity than the packed extraction column and maintain an extraction efficiency for PI and BI of ≥95%. The ability to operate at higher capacity in a sieve tray column will enable reduction in column diameter. Advantageously, the sieve column is not expected to flood at even higher capacities (e.g., greater than 700 gph/sqft). Such high capacities would flood a packed column, but the present inventors have unexpectedly discovered the ability to operate at significantly higher capacities without flooding when a sieve tray column is used, in particular at the desired PA:BI molar ratios and percent solids described above.

The examples show that the process parameters can be adjusted to reduce the amounts of imide anhydride lost to back reaction, which will ultimately increase the overall yield of the desired dianhydride.

This disclosure further encompasses the following aspects.

Aspect 1: A method for producing an aromatic dianhydride, the method comprising: reacting an aromatic diimide with a substituted or unsubstituted phthalic anhydride in an aqueous medium in the presence of an amine exchange catalyst at a reaction temperature of 140 to 250° C. and a reaction pressure of 150 to 300 psig, to provide an aqueous reaction mixture comprising an N-substituted phthalimide, an aromatic tetraacid salt, and at least one of an aromatic triacid salt and an aromatic imide diacid salt; removing the phthalimide from the aqueous reaction mixture by extracting the aqueous reaction mixture with an organic solvent using a single extraction column, wherein the extraction column is a sieve tray extraction column; and converting the aromatic tetraacid salt to the corresponding aromatic dianhydride.

Aspect 2: The method of aspect 1, wherein the purified aromatic dianhydride is obtained in a yield of 75% or greater, preferably 80% or greater.

Aspect 3: The method of aspect 1 or 2, wherein the reacting is at a reaction temperature that is 160 to 200° C., preferably 160 to 180° C., more preferably 170 to 175° C. and a reaction pressure of 200 to 250 psig.

Aspect 4: The method of any one or more of aspects 1 to 3, wherein the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing, preferably phthalic anhydride.

Aspect 5: The method of any one or more of aspects 1 to 4, wherein the exchange catalyst comprises a ($C_{1-20}$ alkyl)-substituted amine, preferably a tri($C_{1-20}$ alkyl)amine, more preferably triethylamine, trimethylamine, or a combination comprising at least one of the foregoing.

Aspect 6: The method of any one or more of aspects 1 to 5, wherein the initial molar ratio of phthalic anhydride to aromatic diimide is 4:1 to 20:1, or 4:1 to 10:1, or 4:1 to 8:1, or 4:1 to 5.5:1, or 4:1 to 5:1.

Aspect 7: The method of any one or more of aspects 1 to 6, wherein the initial molar ratio of amine exchange catalyst to the phthalic anhydride is 1:1 to 2:1.

Aspect 8: The method of any one or more of aspects 1 to 7, wherein the aqueous reaction mixture has a solids content of 10 to 20 weight percent, preferably 13 to 17 weight percent.

Aspect 9: The method of any one or more of aspects 1 to 8, wherein the aromatic diimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing; and the aromatic dianhydride comprises 4,4'-bisphenol A-bis-dianhydride, 3,4'-bisphenol A-bis-dianhydride, 3,3'-bisphenol A-bis-dianhydride, or a combination comprising at least one of the foregoing.

Aspect 10: The method of any one or more of aspects 1 to 9, wherein the organic solvent comprises toluene, xylene, chlorobenzene, ortho-dichlorobenzene, or a combination comprising at least one of the foregoing.

Aspect 11: The method of any one or more of aspects 1 to 10, wherein the volumetric ratio of the organic solvent to aqueous medium is 0.3:1 to 2:1.

Aspect 12: The method of any one or more of aspects 1 to 11, wherein the removing is at an extraction temperature of 100 to 200° C.

Aspect 13: The method of any one or more of aspects 1 to 12, wherein the sieve tray extraction column has a capacity of 220 gallons per hour per square foot or more, or 500 gallons per hour per square foot or more.

Aspect 14: The method of any one or more of aspects 1 to 13, wherein the aqueous reaction mixture is introduced to the sieve tray extraction column using a flow rate of greater than 34 kilograms per hour.

Aspect 15: The method of any one or more of aspects 1 to 14, wherein the dispersed phase holdup is at least 5%, preferably at least 10%.

Aspect 16: An aromatic dianhydride prepared by the method of any one or more of aspects 1 to 15, wherein the aromatic dianhydride has an imide anhydride content of 2 weight percent or less.

The compositions, methods, and articles can alternatively comprise, consist of, or consist essentially of, any appropriate materials, steps, or components herein disclosed. The compositions, methods, and articles can additionally, or alternatively, be formulated so as to be devoid, or substantially free, of any materials (or species), steps, or components, that are otherwise not necessary to the achievement of the function or objectives of the compositions, methods, and articles.

All ranges disclosed herein are inclusive of the endpoints, and the endpoints are independently combinable with each other. "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "an aspect" means that a particular element described in connection with the aspect is included in at least one aspect described herein, and may or may not be present in other aspects. In addition, it is to be understood that the described elements may be combined in any suitable manner in the various aspects.

Unless specified to the contrary herein, all test standards are the most recent standard in effect as of the filing date of this application, or, if priority is claimed, the filing date of the earliest priority application in which the test standard appears.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

Compounds are described using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through carbon of the carbonyl group.

As used herein, the term "hydrocarbyl", whether used by itself, or as a prefix, suffix, or fragment of another term, refers to a residue that contains only carbon and hydrogen. The residue can be aliphatic or aromatic, straight-chain, cyclic, bicyclic, branched, saturated, or unsaturated. It can also contain combinations of aliphatic, aromatic, straight chain, cyclic, bicyclic, branched, saturated, and unsaturated hydrocarbon moieties. However, when the hydrocarbyl residue is described as substituted, it may, optionally, contain heteroatoms over and above the carbon and hydrogen members of the substituent residue. Thus, when specifically described as substituted, the hydrocarbyl residue can also contain one or more carbonyl groups, amino groups, hydroxyl groups, or the like, or it can contain heteroatoms within the backbone of the hydrocarbyl residue. The term "alkyl" means a branched or straight chain, unsaturated aliphatic hydrocarbon group, e.g., methyl, ethyl, n-propyl, i-propyl, n-butyl, s-butyl, t-butyl, n-pentyl, s-pentyl, and n- and s-hexyl. "Alkenyl" means a straight or branched chain, monovalent hydrocarbon group having at least one carbon-carbon double bond (e.g., ethenyl (—HC=CH$_2$)). "Alkoxy" means an alkyl group that is linked via an oxygen (i.e., alkyl-O—), for example methoxy, ethoxy, and sec-butyloxy groups. "Alkylene" means a straight or branched chain, saturated, divalent aliphatic hydrocarbon group (e.g., methylene (—CH$_2$—) or, propylene (—(CH$_2$)$_3$—)). "Cycloalkylene" means a divalent cyclic alkylene group, —C$_n$H$_{2-x}$, wherein x is the number of hydrogens replaced by cyclization(s). "Cycloalkenyl" means a monovalent group having one or more rings and one or more carbon-carbon double bonds in the ring, wherein all ring members are carbon (e.g., cyclopentyl and cyclohexyl). "Aryl" means an aromatic hydrocarbon group containing the specified number of carbon atoms, such as phenyl, tropone, indanyl, or naphthyl. "Arylene" means a divalent aryl group. "Alkylarylene" means an arylene group substituted with an alkyl group. "Arylalkylene" means an alkylene group substituted with an aryl group (e.g., benzyl). The prefix "halo" means a group or compound including one more of a fluoro, chloro, bromo, or iodo substituent. A combination of different halo groups (e.g., bromo and fluoro), or only chloro groups can be present. The prefix "hetero" means that the compound or group includes at least one ring member that is a heteroatom (e.g., 1, 2, or 3 heteroatom(s)), wherein the heteroatom(s) is each independently N, O, S, Si, or P. "Substituted" means that the compound or group is substituted with at least one (e.g., 1, 2, 3, or 4) substituents that can each independently be a C$_{1-9}$ alkoxy, a C$_{1-9}$ haloalkoxy, a nitro (—NO$_2$), a cyano (—CN), a C$_{1-6}$ alkyl sulfonyl (—S(=O)$_2$-alkyl), a C$_{6-12}$ aryl sulfonyl (—S(=O)$_2$-aryl) a thiol (—SH), a thiocyano (—SCN), a tosyl (CH$_3$C$_6$H$_4$SO$_2$—), a C$_{3-12}$ cycloalkyl, a C$_{2-12}$ alkenyl, a C$_{5-12}$ cycloalkenyl, a C$_{6-12}$ aryl, a C$_{7-13}$ arylalkylene, a C$_{4-12}$ heterocycloalkyl, and a C$_{3-12}$ heteroaryl instead of hydrogen, provided that the substituted atom's normal valence is not exceeded. The number of carbon atoms indicated in a group is exclusive of any substituents. For example —CH$_2$CH$_2$CN is a C$_2$ alkyl group substituted with a nitrile.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

What is claimed is:

1. A method for producing an aromatic dianhydride, the method comprising:
    reacting an aromatic diimide with a substituted or unsubstituted phthalic anhydride in an aqueous medium in the presence of an amine exchange catalyst at a reaction temperature of 140 to 250° C. and a reaction pressure of 150 to 300 psig, to provide an aqueous reaction mixture comprising an N-substituted phthalimide, an aromatic tetraacid salt, and at least one of an aromatic triacid salt and an aromatic imide diacid salt;
    removing the phthalimide from the aqueous reaction mixture by extracting the aqueous reaction mixture with an organic solvent using a single extraction column, wherein the extraction column is a sieve tray extraction column; and
    converting the aromatic tetraacid salt to the corresponding aromatic dianhydride.

2. The method of claim 1, wherein the purified aromatic dianhydride is obtained in a yield of 75% or greater.

3. The method of claim 1, wherein the reacting is at a reaction temperature that is 160 to 200° C. and a reaction pressure of 200 to 250 psig.

4. The method of claim 1, wherein the substituted or unsubstituted phthalic anhydride comprises phthalic anhydride, 3-halophthalic anhydride, 4-halophthalic anhydride, 3-nitrophthalic anhydride, 4-nitrophthalic anhydride, or a combination comprising at least one of the foregoing.

5. The method of claim 1, wherein the exchange catalyst comprises a (C$_{1-20}$ alkyl)-substituted amine.

6. The method of claim 1, wherein the initial molar ratio of phthalic anhydride to aromatic diimide is 4:1 to 20:1.

7. The method of claim 1, wherein the initial molar ratio of amine exchange catalyst to the phthalic anhydride is 1:1 to 2:1.

8. The method of claim 1, wherein the aqueous reaction mixture has a solids content of 10 to 20 weight percent.

9. The method of claim 1, wherein
    the aromatic diimide comprises 4,4'-bisphenol A-bis-N-methylphthalimide, 3,4'-bisphenol A-bis-N-methylphthalimide, 3,3'-bisphenol A-bis-N-methylphthalimide, or a combination comprising at least one of the foregoing; and
    the aromatic dianhydride comprises 4,4'-bisphenol A-bis-dianhydride, 3,4'-bisphenol A-bis-dianhydride, 3,3'-bisphenol A-bis-dianhydride, or a combination comprising at least one of the foregoing.

10. The method of claim 1, wherein the organic solvent comprises toluene, xylene, chlorobenzene, ortho-dichlorobenzene, or a combination comprising at least one of the foregoing.

11. The method of claim 1, wherein the volumetric ratio of the organic solvent to aqueous medium is 0.3:1 to 2:1.

12. The method of claim 1, wherein the removing is at an extraction temperature of 100 to 200° C.

13. The method of claim 1, wherein the sieve tray extraction column has a capacity of 220 gallons per hour per square foot or more.

14. The method of claim 1, wherein the aqueous reaction mixture is introduced to the sieve tray extraction column using a flow rate of greater than 34 kilograms per hour.

15. The method of claim 1, wherein the dispersed phase holdup is at least 5%.

16. An aromatic dianhydride prepared by the method of claim 1, wherein the aromatic dianhydride has an imide anhydride content of 2 weight percent or less.

* * * * *